United States Patent [19]
Thompson et al.

[11] Patent Number: 5,935,962
[45] Date of Patent: Aug. 10, 1999

[54] USE OF $\alpha_1$-ADRENORECEPTOR ANTAGONISTS IN THE PREVENTION AND TREATMENT OF CANCER

[75] Inventors: Timothy C. Thompson; Guang Yang, both of Houston, Tex.; Michael G. Wyllie, New York, N.Y.

[73] Assignee: Baylor College of Medicine and Pfizer, Inc.

[21] Appl. No.: 08/827,137

[22] Filed: Mar. 27, 1997

Related U.S. Application Data

[60] Provisional application No. 60/014,228, Mar. 27, 1996.

[51] Int. Cl.⁶ .................................................. A61K 31/50
[52] U.S. Cl. ............................................................ 514/254
[58] Field of Search ...................... 514/254, 249

[56] References Cited

U.S. PATENT DOCUMENTS

| | | | |
|---|---|---|---|
| 4,188,390 | 2/1980 | Campbell | 514/254 |
| 4,758,569 | 7/1988 | Swindell | 514/254 |
| 5,523,094 | 6/1996 | Andrieu et al. | 514/258 |

FOREIGN PATENT DOCUMENTS

| | | |
|---|---|---|
| 0 564 093 | 10/1993 | European Pat. Off. . |
| 0 582 502 | 2/1994 | European Pat. Off. . |
| WO 95 28157 | 10/1995 | WIPO . |
| WO 95 28932 | 11/1995 | WIPO . |

OTHER PUBLICATIONS

Biochemical and Biophysical Research Communications, vol. 185, No. 1, 1992, pp. 176–184.
Carcinogenesis, vol. 10, No. 1, 1989, pp. 73–78.
BR. J. Cancer, vol. 64, 1991, pp. 683–688.
Berkow et al. "The Merck Manual", 1992, pp. 1736–1737.

*Primary Examiner*—Jerome D. Goldberg
*Attorney, Agent, or Firm*—Connolly & Hutz

[57] ABSTRACT

A method for treating or preventing a cancer in a mammal which comprises administering to said mammal an amount of a drug, comprising an $\alpha_1$-adrenoreceptor antagonist or pharmaceutically acceptable acid addition salt thereof, effective for treating or preventing the cancer.

7 Claims, No Drawings

USE OF $\alpha_1$-ADRENORECEPTOR ANTAGONISTS IN THE PREVENTION AND TREATMENT OF CANCER This application is a continuation of Provisional Application No. 60/014,228 filed Mar. 27, 1996.

BACKGROUND OF THE INVENTION

1. Field of the Invention

This invention relates to the use of $\alpha_1$-adrenoreceptor antagonists, or pharmaceutically acceptable acid addition acid addition salts thereof, for treating or preventing the formation of cancers. More particularly, it relates to a method for preventing the formation of, or reducing, such cancers in mammals by administering to said mammals an effective amount of an $\alpha_1$ - adrenoreceptor antagonist or pharmaceutically acceptable acid addition salt thereof.

2. General Background

Cancer incidence is now at a level whereby it is predicted that it will be the primary cause of death in the United States by the year 2000. Although some advances have been made in the treatment of cancers individual mortality, in those over the age of 65, has not changed. Prostate cancer, predominantly in males over sixty-five years of age, has become an ever increasing problem in the developed countries of the world where men are living to older ages. Among males it is now the second greatest cause of cancer deaths. In the United States it was the cause of about 3% of all deaths (about 35000) in 1993. It has been predicted that the number of prostate cancer patients will increase dramatically over the next decade due to demographic changes in the population.

Early studies of phenoxybenzamine (a nonselective $\alpha_1$ and $\alpha_2$ adrenoreceptor antagonist) and prazosin (a selective $\alpha_1$ adrenoreceptor antagonist) were effective in the treatment of smooth muscle effects of BPH with the selective $\alpha_1$ agent producing fewer and more tolerable side effects than the nonselective phenoxybenzamine.

Kenny, B. et al. ($\alpha_1$-Adrenoreceptor Antagonists As Treatments For Benign Prostatic Hyperplasia, *Exp. Opin. Invest. Drugs*, (1995), 4(10), 915–23), incorporated herein in its entirety by reference) have discussed the use of a number of $\alpha_1$-adrenoreceptor antagonists, such as terazosin, doxazosin, indoramin and tamsulosin for the treatment of symptoms of BPH. However, they did not suggest that $\alpha_1$-adrenoreceptor antagonists could be used to prevent the formation of cancers or, if formed, treatment thereof to decrease the tumors.

Kaplan, S. A. et al, (*Urology*, 46(4), 1995, 512–17), Kirby, R. S. (*Urology*, 46(2), 1995, 182–6) and Fawzy, A. et al. (The Journal of Urology, 154, 105–9 (1995)) have discussed the effect of doxazosin on the blood pressure of normotensive men who are being treated with doxazosin for mediation of the dynamic component of smooth muscle prostate outflow obstruction.

Doxazosin, 4-amino-2-[4-(1-4-benzodioxan-2-carbonyl) piperazin-1-yl]-6,7-dimethoxyquinazoline and its pharmaceutically acceptable acid addition acid addition salts, are described in U.S. Pat. No. 4,188,390 together with their use as regulators of the cardiovascular system, especially in the treatment of hypertension.

U.S. Pat. No. 4,758,569 claims the use of doxazosin in retarding development of atherosclerosis in a mammal. The use of trimazosin or a pharmaceutically acceptable acid salt thereof, for retarding atherosclerosis is described and claimed in U.S. Pat. No. 4,582,832.

U.S. Pat. Nos. 4,868,216 and 4,987,152 claim the use of tamsulosin and its hydrochloride for producing $\alpha_1$-adrenoreceptor antagonistic action, or treating urinary tract dysfunction, respectively, in a host.

$\alpha_1$-Adrenoreceptor antagonists such as 2,4,6,7-tetrasubstituted quinazolines are disclosed in U.S. Pat. Nos. 3,511,836, 4,001,237 and 4,188,390 for use as hypertensive agents. U.S. Pat. No. 4,112,097 also claims the use of terazosin, and its tetrahydropyran-2-carbonyl homologue, for treatment of hypertension in mammals.

Despite the many patents and studies, such as those above, relating to the use of $\alpha_1$-adrenoreceptor antagonists in the treatment of hypertension, atherosclerosis, urinary tract dysfunction and smooth muscle tone in BPH there have been no report of any teaching or suggestion that $\alpha_1$-adrenoreceptor antagonists, metabolites or their pharmaceutically acceptable acid addition acid addition salts could be used to prevent the formation of, or reduce cancerous tumors in a mammal.

SUMMARY OF THE INVENTION

It has now been found that drugs comprising $\alpha_1$-adrenoreceptor antagonists or their pharmaceutically acceptable acid addition salts when administered to a mammal, prior to the onset of a cancer can prevent its formation or, after the onset of the cancer, can reduce the condition. Cancers which are susceptible to such treatments include the solid tumor cancers such as, prostatic, bladder, renal, breast and colon, and vascular cancers such as non-Hodgkin's lymphoma.

More specifically, the drugs when administered in therapeutically effective doses prevent formation of cancer or if cancer is already present they increase the rate of apoptosis of the abnormal cells. Preferably the $\alpha 1$-adrenoreceptor antagonists are selected from the group comprising alfuzosin, indoramin, terazosin, bunazosin, doxazosin and its 6'- and 7'- hydoxy metabolites, prazosin, tamsulosin, abanoquil, Recordati 15/2739 (trademark), RS 17053 (trademark), SL 89.0591 (trademark), other $\alpha_1$-adrenoreceptor antagonists mentioned by Kenny et al. (Id. at pages 917 and 919–20) and the like.

DETAILED DESCRIPTION OF THE INVENTION

This invention relates to the use of drugs comprising $\alpha_1$-adrenoreceptor antagonists, their metabolites and their pharmaceutically acceptable acid addition salts to prevent the formation of cancers or, if formed, treatment thereof to decrease the tumors. urinary cancers. $\alpha_1$-Adrenoreceptor antagonists useful in the practice of the invention include alfuzosin, indoramin, terazosin, bunazosin, doxazosin and its 6'- and 7'- hydoxy metabolites, prazosin, tamsulosin and the like and their pharmaceutically acceptable acid addition salts. Most preferred $\alpha_1$-adrenoreceptor antagonists are doxazosin and its 6'- and 7'- hydoxy metabolites and their pharmaceutically acceptable acid addition acid addition salts.

The preferred pharmaceutically acceptable acid addition salts, of the $\alpha_1$-adrenoreceptor antagonists, for use in the practice of the invention are those prepared from mineral acids such as hydrochloric, sulfuric, nitric and phosphoric; organic acids such as sulfonic acids, e. g. benzenesulfonic (besylic), p-toluenesulfonic (PtSA, tosylic), methanesulfonic (MSA, mesylic) and trifluoromethanesulfonic (triflic); carboxylic acids e.g., acetic, proprionic, benzoic, citric, tartaric, maleic, fumaric, succinic and malic. In the case of polybasic acids such as sulfuric and phosphoric the salts may be formed from any of the ionic forms thereof, e.g., in the case of phosphoric acid from its mono- di- and tribasic forms. A most preferred acid is hydrochloric.

In the treatment of urinary cancers the $\alpha_1$-adrenoreceptor antagonists, or their pharmaceutically acceptable acid addition acid addition salts (hereafter the 'active compounds) can be administered via oral or parenteral, including transdermal, routes. However, it is generally preferred to administer the active compounds orally. The active compounds are most desirably administered in doses ranging from about 0.01 to about 2.0 mg/kg per day. However, variations will generally be necessary depending upon the weight of the patient. The proper dose for treating or preventing the formation of a cancer in a specific patient will easily be determined by one who is skilled in the art of prescribing and/or administering such compounds. In the case of doxazosin, for instance, the effective dosages, for treating hypertension, are from about 0.02 to about 0.60 mg/kg body weight per day with the preferred maximal oral range in man being about 0.15 to about 0.30 mg/kg body weight per day. It is to be understood that other variations may arise which depend upon the species of the patient and its individual response to a particular active compound and formulation for the time period and interval of administering the composition. It is sometimes found that dosages below the aforesaid lower levels are adequate and at other times larger dosages may be required, and administered without undesirable side effects. In the latter case the higher dosages may must be divided into smaller doses which are administered throughout the day or the drug may be administered in a controlled release formulation.

For purposes of oral administration, tablets containing excipients such as sodium citrate, calcium carbonate and dicalcium phosphate may be employed along with various disintegrants such as a starch, preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed in soft elastic and hard-filled gelatin capsules. When aqueous suspensions and/ or elixirs are desired for oral administration, the active compound may be combined with various sweetening or flavoring agents, coloring matter and, if so desired, emulsifying and/or suspending agents, together with diluents such as water, ethanol, propylene glycol, glycerin and combinations thereof.

Although the preferred mode of administration of the active compound is oral they may be administered parenterally as well.

For purposes of parenteral administration, solutions of the active compounds in sesame or peanut oil or in aqueous propylene glycol may be employed, as well as sterile aqueous solutions of the corresponding water soluble acid addition salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld (trademark), the Chamberland (trademark) and the Asbestos Disk-Metal Seitz (trademark) filter, wherein the fluid is sucked into a sterile container with the aid of a suction pump. Needless to say, the necessary steps should be taken throughout the preparation of these injectable solutions to insure that the final products are obtained in a sterile condition.

The active compounds can also be administered transdermally. For purposes of transdermal administration, the dosage form of the particular compound may include, by way of example, solutions, lotions, ointments, creams, gels, suppositories, rate-limiting sustained release formulations and devices therefor. Such dosage forms comprise the particular compound and may include ethanol, water, penetration enhancer and inert carriers such as gel-producing materials, mineral oil, emulsifying agents, benzyl alcohol and the like. Specific transdermal flux enhancing compositions are disclosed in pending U.S. patent application Ser. No. 925,641 which is assigned to the assignee of this invention, the teachings of which are incorporated herein by reference.

The effect of the drugs on apoptosis of the cancerous cells is determined by means of the mouse prostatic reconstitution (MPR) system. (See Slawin et al, *Cancer Research,* 53, 4461–5 (1993)).

To determine if TFG-β1 overexpression is involved in cancer pathogenesis we employ a model using the MPR system. Recombinant retroviruses carrying mouse TGF-β1 cDNSs (Babe TGF-β1 Gal and Babe TGF-β1Neo) or a control virus (BAG-a) were used to infect urogenital sinus (UGS) cells dissociated from 17-day old C57βL/6 mouse embryos. The UGS cells were then implanted under the renal capsules of adult male mice, where they develop into cancerous tissues under normal conditions. Relative to BAG-a controls, Babe TGF-β1 infected MPRs contained increased numbers of focal lesions composed of benign epithelial hyperplasia as well as stromal cell hyperplasia. Immunostaining of these lesions with K-14 and tGF-β1 antisera revealed prodominantly basal epithelial cells surrounded by hyperplastic stroma with TGF-β1 accumulation. In addition, significantly increased numbers of neuronal cells, mostly catecholaminergic, were also associated with Babe TGF-β1 infected MPRs.

Using the above model the effects of doxazosin, an $\alpha_1$-adrenoceptor blocker, on formation or destruction of cancerous lesions was evaluated.

I claim:

1. A method for treating or preventing cancer sensitive to the compound below in a mammal in need thereof which comprises administering to said mammal an $\alpha_1$-adrenoreceptor antagonist selected from the group consisting of doxazosin, its 6'-hydroxy metabolite, its 7'-hydroxy metabolite and a pharmaceutically acceptable acid addition salt thereof, in an effective amount for treating or preventing said cancer.

2. The method according to claim 1 wherein the $\alpha_1$-adrenoreceptor antagonist is the 6'-hydoxy metabolite of doxazosin.

3. The method according to claim 1 wherein the $\alpha_1$-adrenoreceptor antagonist is the 7'-hydoxy metabolite of doxazosin.

4. The method according to claim 1 wherein the $\alpha_1$-adrenoreceptor antagonist is administered orally.

5. The method according to claim 1 wherein the $\alpha_1$-adrenoreceptor antagonist is administered intraperitoneally.

6. The method according to claim 1 wherein the $\alpha_1$-adrenoreceptor antagonist is administered transdermally.

7. The method according to claim 1 wherein the $\alpha_1$-adrenoreceptor antagonist is administered parenterally.

* * * * *